United States Patent
Tran et al.

(10) Patent No.: US 9,176,039 B2
(45) Date of Patent: Nov. 3, 2015

(54) METHOD AND SYSTEMS FOR DETERMINING HYDROGEN EMBRITTLEMENT

(71) Applicant: The Boeing Company, Chicago, IL (US)

(72) Inventors: Luong Minh Tran, Lakewood, WA (US); Matthias P. Schriever, Kent, WA (US)

(73) Assignee: The Boeing Company, Chicago, IL (US)

( * ) Notice: Subject to any disclaimer, the term of this patent is extended or adjusted under 35 U.S.C. 154(b) by 219 days.

(21) Appl. No.: 13/780,944

(22) Filed: Feb. 28, 2013

(65) Prior Publication Data

US 2014/0238145 A1    Aug. 28, 2014

(51) Int. Cl.
*G01N 3/20* (2006.01)
*G01N 3/28* (2006.01)
*G01N 33/20* (2006.01)
(Continued)

(52) U.S. Cl.
CPC .. *G01N 3/28* (2013.01); *G01N 3/20* (2013.01); *G01N 33/20* (2013.01); *G01N 17/002* (2013.01); *G01N 19/08* (2013.01); *G01N 2203/0003* (2013.01); *G01N 2203/0023* (2013.01); *G01N 2203/0064* (2013.01); *G01N 2203/0066* (2013.01); *G01N 2203/0067* (2013.01); *G01N 2203/0073* (2013.01); *G01N 2203/0096* (2013.01); *G01N 2203/024* (2013.01); *G01N 2203/027* (2013.01); *G01N 2203/0252* (2013.01); *G01N 2203/0282* (2013.01)

(58) Field of Classification Search
CPC ............. G01N 3/20; G01N 2203/024; G01N 2203/027; G01N 2203/0023; G01N 2203/0066; G01N 2203/0096; G01N 2203/0073; G01N 2203/0064; G01N 17/002; G01N 19/08
USPC ............... 73/849, 856, 821, 818, 825, 86–87, 73/799, 851–854

See application file for complete search history.

(56) References Cited

U.S. PATENT DOCUMENTS

| 3,241,056 A | 3/1966 | Lawrence |
| 3,357,903 A | 12/1967 | Lawrence |
| 3,868,849 A * | 3/1975 | Hunyar ............... 73/854 |

(Continued)

FOREIGN PATENT DOCUMENTS

EP      0230012 A2    7/1987

OTHER PUBLICATIONS

Nilsson et al. "Bending Fatigue Failures in Valve Steel" Internationl Compressor Engineering Conference. 1980. <http://docs.lib.purdue.edu/icec/361/>.*

(Continued)

*Primary Examiner* — Lisa Caputo
*Assistant Examiner* — Jonathan Dunlap
(74) *Attorney, Agent, or Firm* — Armstrong Teasdale LLP

(57) ABSTRACT

A method for use in determining hydrogen embrittlement in a plated sample is provided. The method includes positioning the plated sample between a first holding member and a second holding member, moving the second holding member towards the first holding member to bend the plated sample, and applying a static load to the plated sample for a predetermined duration of time. The static load is applied by bending the plated sample to a distance between the first and second holding members that is a predetermined percentage of a baseline ultimate failure distance of the plated sample.

20 Claims, 7 Drawing Sheets

(51) Int. Cl.
  *G01N 19/08* (2006.01)
  *G01N 17/00* (2006.01)

(56) References Cited

U.S. PATENT DOCUMENTS

| | | | |
|---|---|---|---|
| 4,461,168 A * | 7/1984 | Kobayashi | 73/87 |
| 4,477,778 A | 10/1984 | Lawrence, Jr. | |
| 4,765,871 A | 8/1988 | Hsu et al. | |
| 4,818,632 A | 4/1989 | Hsu et al. | |
| 4,859,291 A | 8/1989 | Takada et al. | |
| 5,505,095 A * | 4/1996 | Raymond | 73/853 |
| 5,549,007 A * | 8/1996 | Raymond | 73/856 |
| 5,585,570 A * | 12/1996 | Raymond | 73/851 |
| 6,120,908 A * | 9/2000 | Papanu et al. | 428/429 |
| 6,918,306 B1 * | 7/2005 | Cavallaro et al. | 73/849 |
| 7,089,802 B2 | 8/2006 | Tran et al. | |
| 8,177,953 B2 * | 5/2012 | Nardi et al. | 205/81 |
| 8,513,020 B2 * | 8/2013 | Hehn et al. | 436/6 |
| 2006/0191352 A1 * | 8/2006 | Lewellen | 73/856 |
| 2010/0147694 A1 * | 6/2010 | Nardi et al. | 205/81 |
| 2012/0009437 A1 | 1/2012 | Tran et al. | |

OTHER PUBLICATIONS

Willan, Hydrogen Embrittlement: A Guide for the Metal Finisher, Omega Research, Inc., available at http://www.omegaresearchinc.com/Publications/metal.html, last visited Jan. 18, 2013.

Hsu, A New Zinc-Nickel Electroplating Process: Alternative to Cadmium Plating, Boeing Materials Technology, Boeing Commercial Airplane Co., Seattle WA, Aug. 21, 1992.

Marioli-Riga et al., Combined Effect of Hydrogen and Corrosion on High Strength Aircraft Structures under Stressed Conditions, RTO AVT Workshop, Corfu, Greece, Oct. 7-8, 1998, pp. 12-1 to 12-10.

* cited by examiner

METHOD AND SYSTEMS FOR DETERMINING HYDROGEN EMBRITTLEMENT

BACKGROUND

The field of the present disclosure relates generally to hydrogen embrittlement, and more specifically, to methods and systems for testing for potential hydrogen embrittlement.

Hydrogen embrittlement refers to a process that causes a metal or metal alloy, such as steel, to become brittle and susceptible to fracture when exposed to a quantity of hydrogen and subjected to a tensile load. As used herein, the term "metal" may refer to a single metal or a metal alloy. Hydrogen embrittlement generally occurs when hydrogen atoms diffuse through the crystalline structure (i.e., matrix) of a metal resulting in an increased pressure within the metal matrix. The increased pressure can adversely affect characteristics of metal such as ductility and tensile strength. At least some known sources of hydrogen atoms are electroplating solutions, pickling solutions, phosphating solutions, paint-stripping solutions, cleaning solutions, and the like.

In at least some known electrodeposition processes, a metal substrate cathode and a plating material anode are submerged in a plating solution. Electric current is applied to the anode and cathode to deposit a layer of plating material on the surface of the metal substrate via the plating solution. After a desired amount of plating material has been deposited on the metal substrate, the substrate may then be heated to facilitate removing hydrogen trapped in the steel substrate beneath the plating material. Metal substrates also generally have organic surface contaminants, which if not properly cleaned prior to plating, may contaminate the plating solution. As such, prolonged use of the plating solution may affect the quality of the plated sample due to the contaminants. For example, an increased contaminant concentration in the plating solution may decrease the porosity of the plating layer, thereby limiting the amount of hydrogen removed from plated metals during the post-deposition heating process, which is commonly referred to as Hydrogen Embrittlement Relief Baking.

One known method of determining the porosity level of plating solution involves performing a series of stress tests on samples plated using a plating solution. In one known stress test, plated samples fabricated from a rigid metal substrate, such as AISI 4340 steel, are subjected to tensile stress at 75 percent of their respective ultimate failure load for a predetermined duration. The plating solution is determined to be contaminated if the plated sample breaks before the end of the predetermined duration. However, these known test methods are generally time-consuming, can take up to 200 hours to complete, and thus make it difficult to determine the contamination level of plating solution in real-time.

BRIEF DESCRIPTION

In one aspect, a method for use in determining hydrogen embrittlement in a plated sample is provided. The method includes positioning the plated sample between a first holding member and a second holding member, moving the second holding member towards the first holding member to bend the plated sample, and applying a static load to the plated sample for a predetermined duration of time. The static load is applied by bending the plated sample to a distance between the first and second holding members that is a predetermined percentage of a baseline ultimate failure distance of the plated sample.

In another aspect, a system for use in determining hydrogen embrittlement in a plated sample is provided. The system includes a frame, a first holding member coupled to the frame, a second holding member coupled to the frame and configured to move relative to the first holding member, and a testing location defined between the first and second holding members. Testing location receives the plated sample and the second holding member moves towards the first holding member to apply a static load to the plated sample by bending the plated sample to a distance between the first and second holding members that is a predetermined percentage of a baseline ultimate failure distance of the plated sample.

In yet another aspect, a system for use in determining hydrogen embrittlement is provided. The system includes a frame, a first holding member coupled to the frame, a second holding member coupled to the frame and configured to move towards the first holding member, a plated sample positioned between the first and second holding members. The plated sample bends when the second holding member moves towards the first holding member to apply a static load to the plated sample by bending the plated sample to a distance between the first and second holding members that is a predetermined percentage of a baseline ultimate failure distance of said plated sample.

DETAILED DESCRIPTION

Implementations of the present disclosure relate to a testing system and methods for determining hydrogen embrittlement in one or more plated metal test samples. The testing system described herein includes a frame, a first holding member coupled to the frame, and a second holding member coupled to the frame that moves towards the first holding member during operation. In the exemplary implementation, plated samples are positioned between the first and second holding members, and the second holding member moves towards the first holding member to apply a static load to the plated samples by bending the plated sample to a distance that is a predetermined percentage of a baseline ultimate failure distance of the plated sample. The plated samples described herein are fabricated from a flexible metal substrate such as AISI 1095 steel, and moving the second holding member towards the first holding member facilitates bending the plated samples in a bow-like configuration. The presence of hydrogen embrittlement is determined if the plated samples fracture before expiration of a predetermined duration. As such, the testing system described herein is configured to provide a determination of hydrogen embrittlement in real-time. As used herein, "real-time" refers to a duration that is less than about 24 hours and, more specifically, less than about 8 hours.

Figure 1:
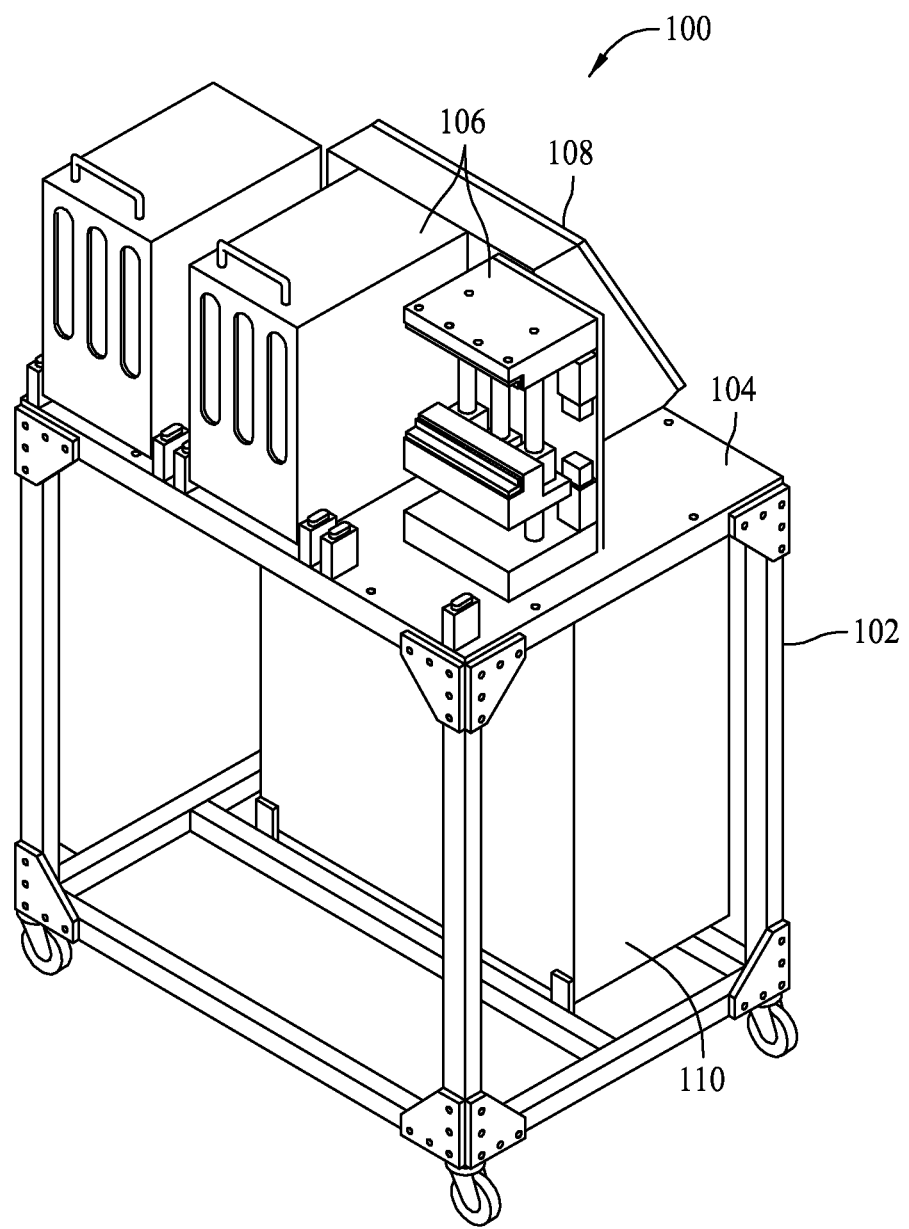
FIG. 1 illustrates a perspective view of an exemplary testing system.
Figure 2:
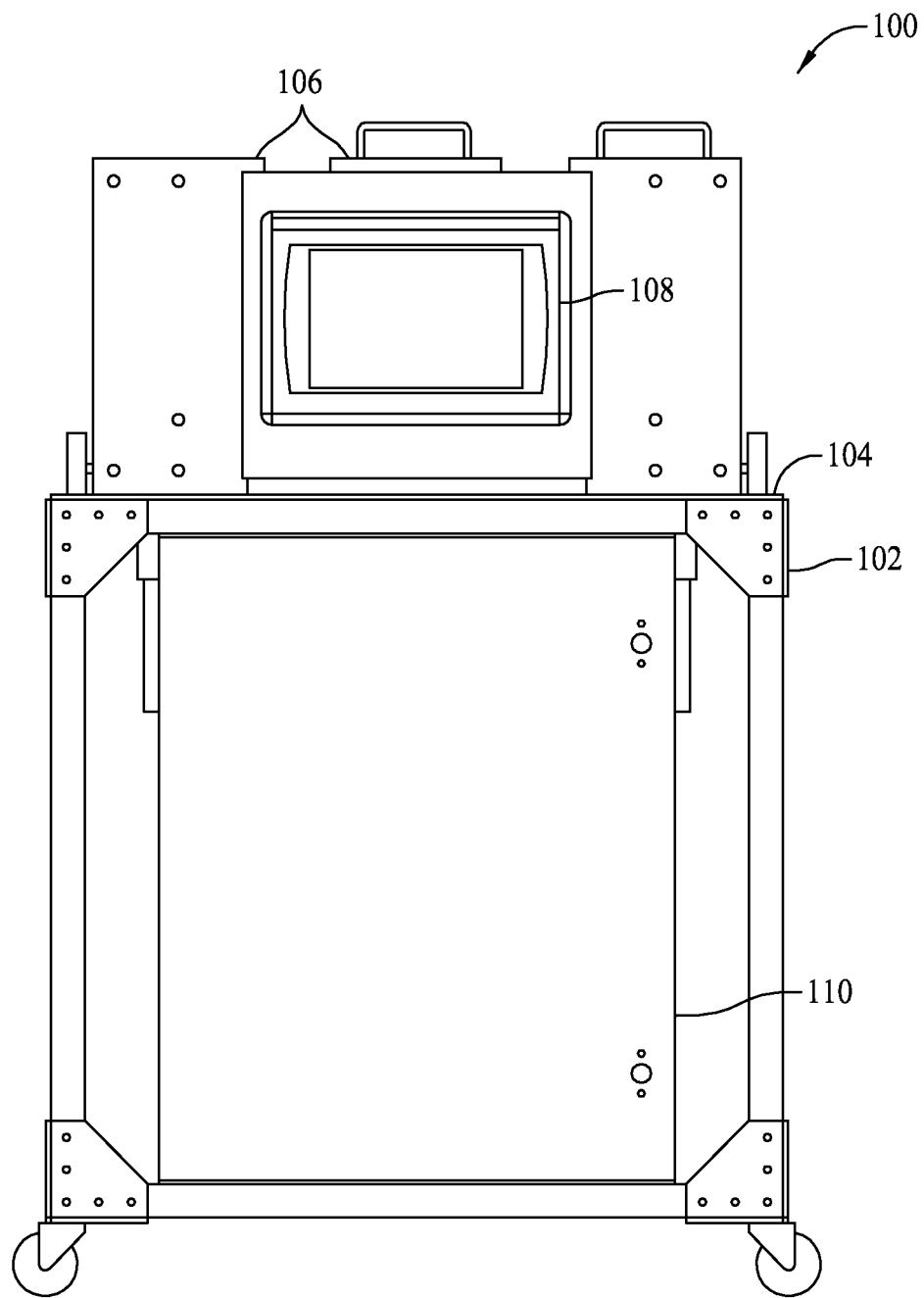
FIG. 2 illustrates a front view of the testing system shown in FIG. 1.

FIGS. 1 and 2 illustrate an implementation of testing system 100. In the exemplary implementation, testing system 100 includes a base 102, a work surface 104 coupled to base 102, a plurality of vise systems 106 coupled to work surface 104, and a display panel 108 coupled to work surface 104. Display panel 108 and vise systems 106 may be coupled in communication with a control system 200 (not shown in FIG. 1) that control the operation of testing system 100. In some implementations, control system 200 may be housed within an electrical box 110.

Display panel 108 may be any suitable device that enables testing system 100 to function as described herein. Exemplary suitable display panels 108 include, but are not limited to, a liquid crystal display (LCD), an organic light emitting diode (OLED) display, a cathode ray tube (CRT) display, an "electronic ink" display, and the like. In the exemplary implementation, display panel 108 is a touch screen device that enables display panel 108 to function as an output device and an input device. In alternative implementations, testing system 100 may include one or more input devices separate from display panel 108 such as, for example, a keyboard, a pointing device, a mouse, a stylus, an audio input device, and the like.

Figure 3:
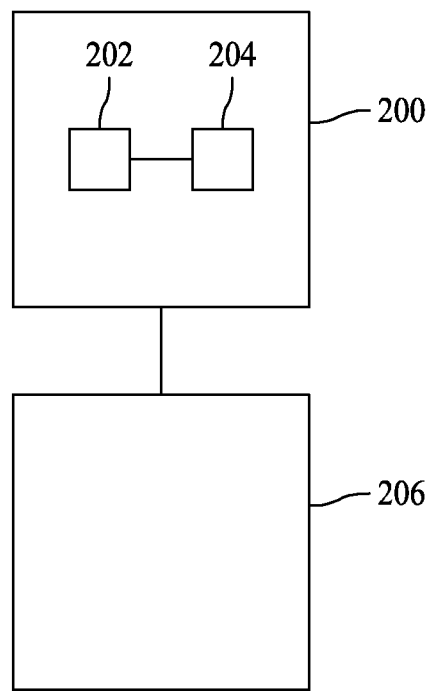
FIG. 3 illustrates a schematic diagram of an exemplary control system that may be used with the testing system shown in FIG. 1.

FIG. 3 is a schematic diagram of an exemplary control system 200. As illustrated, control system 200 includes a memory device 202 and a processor 204 coupled to memory device 202 for use in executing operating instructions to be used by testing system 100 (shown in FIG. 1). In the exemplary implementation, memory device 202 and/or processor 204 are programmed to perform one or more operations described herein such as controlling the operation of testing system 100. For example, processor 204 may be programmed by encoding an operation as one or more executable instructions stored in memory device 202.

Processor 204 may include one or more processing units (e.g., in a multi-core configuration). As used herein, the term "processor" is not limited to integrated circuits and may include any of a controller, a microcontroller, a microcomputer, a programmable logic controller (PLC), an application specific integrated circuit, and other programmable circuits. Memory device 202 may also include one or more computer readable media such as, without limitation, dynamic random access memory (DRAM), static random access memory (SRAM), a solid state disk, and/or a hard disk.

In the exemplary implementation, memory device 202 includes one or more devices (not shown) that enable information such as executable instructions and/or other data to be selectively stored and retrieved. In the exemplary implementation, such data may include, but is not limited to, calibration procedures for testing system 100, testing procedures for testing system 100, a rate of movement for the second holding member 416 (not shown in FIG. 3), instructions to activate one or more of the plurality of vise systems 106 (shown in FIG. 1), and the like. Alternatively, control system 200 may be configured to use any algorithm and/or program that enables the methods and systems to function as described herein.

In some implementations, control system 200 is coupled to a timing device 206. Timing device 206 monitors plated samples 300 (not shown in FIG. 2) during operation, and determines if and/or when plated samples 300 fracture when the static load is applied. As such, the presence of hydrogen embrittlement is determined when the static load is applied to plated samples 300 and they fracture before expiration of the predetermined duration.

Figure 4:
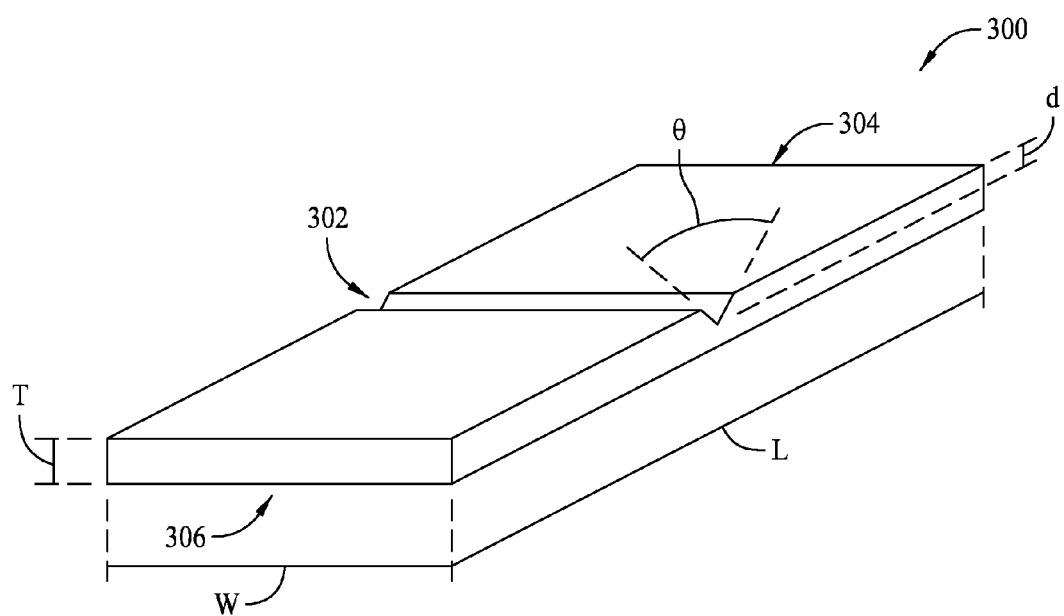
FIG. 4 is a perspective view of an exemplary plated sample that may be used in the testing system shown in FIG. 1.

As illustrated in FIG. 4, plated sample 300 may have any suitable dimensions (i.e., length, width, and thickness) that enable testing system 100 to function as described herein. More specifically, the dimensions of plated sample 300 may be based on the material used to fabricate plated sample 300, and/or the predetermined duration used to determine the occurrence of hydrogen embrittlement in plated samples 300. Plated sample 300 has a first end 304, a second end 306, a length L extending therebetween, a width W, and a thickness T. In some implementations, length L is about 8 inch, width W is about 0.5 inch, and thickness T is about 0.03 inch. It should also be understood that plated sample 300 is not limited to the rectangular shape shown, and may be any suitable shape that enables testing system 100 to function as described herein. Moreover, in the exemplary implementation, plated sample 300 includes a notch 302 positioned at about half of length L of plated sample 300. In the exemplary implementation, notch 302 is defined in the metal substrate before plating, has a depth d defined within a range of about 0.003 inch to about 0.005 inch, and has a notch angle $\theta$ of about 60°.

In the exemplary implementation, plated sample 300 is fabricated from a metal substrate (not shown) with plating material deposited thereon. However, plated sample 300 may be fabricated from any suitable material(s) that enables testing system 100 to function as described herein. The metal substrate may have any suitable physical properties that enable plated sample 300 to be bent as described herein when subjected to a load. An exemplary substrate material includes, but is not limited to, AISI 1095 steel. In some implementations, the metal substrate is heat treated to achieve a Rockwell hardness level defined within a range of from about 56 HRC to about 59 HRC by double tempering with a final process temperature of about 450° F. The metal substrate may then be plated using any suitable solution that enables testing system 100 to function as described herein. Exemplary plating solutions include, but are not limited to, a cadmium solution, a zinc-nickel solution, and the like. In the exemplary implementation, plating material is deposited onto a surface of the metal substrate at a thickness defined within a range of about 0.0005 inch to about 0.0008 inch.

Figure 5:
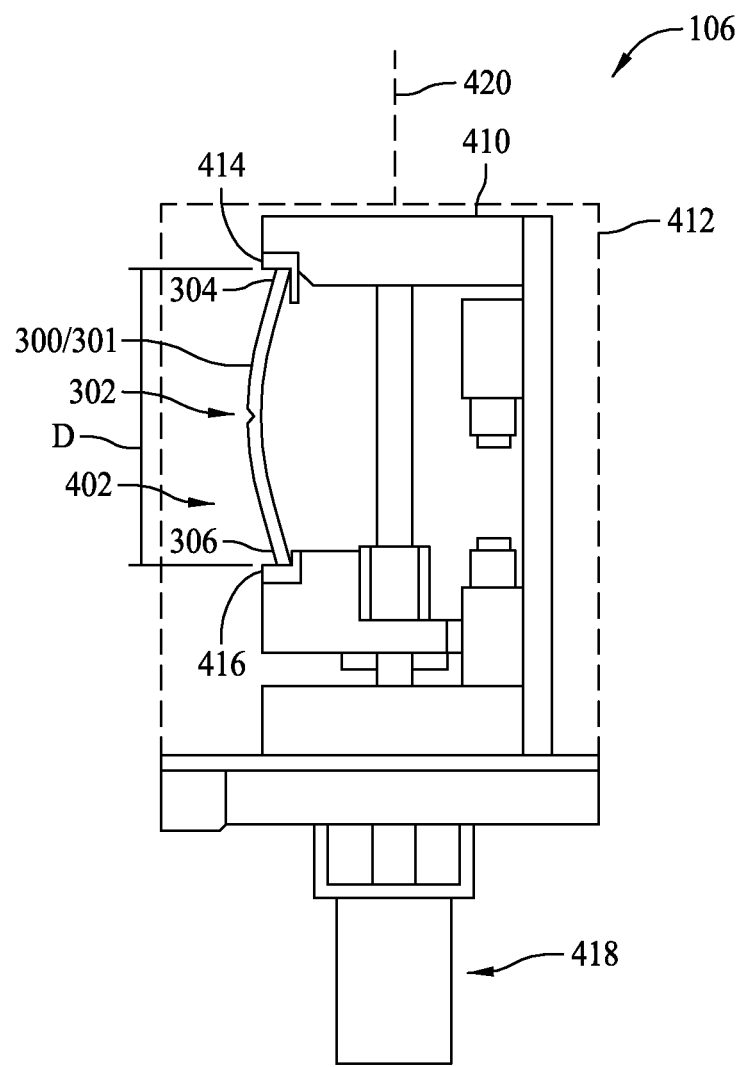
FIG. 5 illustrates a side view of the vise system shown in FIG. 1 in a first operational position.
Figure 6:
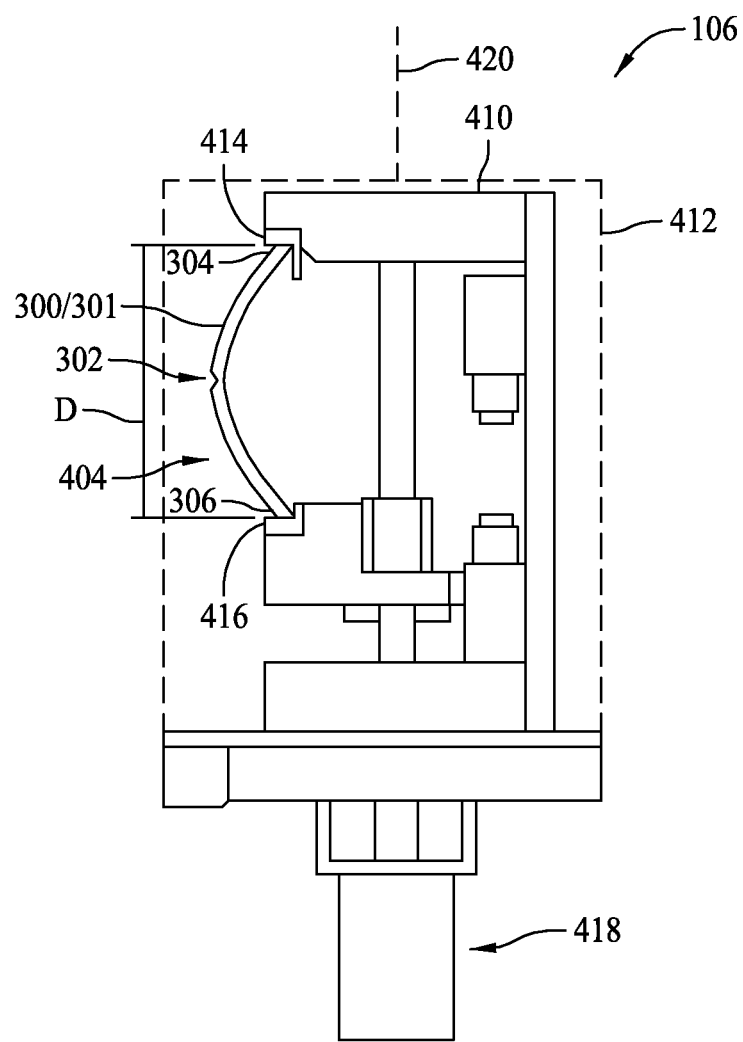
FIG. 6 illustrates a side view of the vise system shown in FIG. 1 in a second operational position.

FIG. 5 illustrates a side view of vise system 106 in a first operational position 402, and FIG. 6 illustrates a side view of vise system 106 in a second operational position 404. As illustrated, vise system 106 includes a frame 410, a protective cover 412 positioned about frame 410, a first holding member 414 coupled to frame 410, a second holding member 416 coupled to frame 410, and a motor 418 that moves vise system 106 from first operational position 402 to second operational position 404. More specifically, motor 418 is configured to move second holding member 416 substantially linearly along translational axis 420 towards first holding member 414 at a rate of movement. In an alternative implementation, motor 418 is configured to move first holding member 414 and second holding member 416 towards each other simultaneously.

In operation, a plurality of unplated samples 301 are fabricated and used to calibrate testing system 100 (shown in FIG. 1) to determine a baseline ultimate failure load for plated samples 300. In the exemplary implementation, testing system 100 is calibrated by moving second holding member 416 into first operational position 402 and loading unplated sample 301 into vise system 106 with notch 302 facing outward from frame 410. Unplated sample 301 is positioned between first holding member 414 and second holding member 416 such that first end 304 contacts first holding member 414 and second end 306 contacts second holding member 416. In first operational position 402, second holding member 416 is positioned a distance D from first holding member 414, where distance D is slightly less than length L (shown in FIG. 4) of unplated sample 301. For example, when unplated sample 301 has a length of about 8 inch, second holding member 416 is moved towards first holding member 414 to facilitate reducing distance D to about 7.9 inch. As such, in the exemplary implementation, unplated sample 301 is bent into a curved (e.g., bow-like) configuration and loaded into vise system 106.

After loading unplated samples 301 into vise system 106, protective cover 412 may be positioned about frame 410, and second holding member 416 is operated to move towards first holding member 414 at the rate of movement until unplated samples 301 fracture to determine the baseline ultimate failure distance D for plated samples 300. More specifically, the baseline ultimate failure distance D is determined using the following equation:

$$TSL = \left[\frac{(TSL - FBD) * (\% \ OBD * 100)}{100}\right] = \% \ of \ FBD,$$

, where TSL is length L (shown in FIG. 4), FBD is the average distance D that fractures unplated samples 301, and OBD is length L minus the average distance D that fractures unplated samples 301. As such, a distance D (% of FBD) is determined that results in a predetermined percentage of the baseline ultimate failure for a given batch of plated samples 300. In the exemplary implementation, the predetermined percentage (% OBD) is 75 percent of the baseline ultimate failure distance D for the plated samples 300 used to calibrate testing system 100.

In the exemplary implementation, protective cover 412 is configured to prevent plated samples 300 and/or unplated samples 301 from discharging from vise system 106 during fracture. In some implementations, control system 200 (shown in FIG. 2) is operable to disable the movement of second holding member 416 if protective cover 412 is not positioned about frame 410. For example, in one implementation, protective cover 412 activates a switch (not shown) when positioned about frame 410 that enables second holding member 416 to move towards first holding member 414. In some implementations, protective cover 412 includes compartments (not shown) associated with each sample 300 and/or 301 to separate them from one another in case of projectiles from fracture striking other samples 300 and/or 301.

In some implementations, second holding member 416 may be operated to move towards first holding member 414 continuously, iteratively, and/or combinations thereof. Moreover, second holding member 416 may be operated to move towards first holding member 414 at any suitable rate of movement that enables testing system 100 to function as described herein. The rate of movement used may facilitate bending unplated sample 301 without fracture until a desired distance D is reached. In some implementations, the rate of movement is from about 0.1 inch per every 3 minutes to about 0.1 inch per minute.

After testing system 100 has been calibrated, testing system 100 is ready to determine hydrogen embrittlement in plated samples 300. In the exemplary implementation, plated samples 300 are fabricated as described above, subjected to a Hydrogen Embrittlement Relief Baking (HERB) process, and loaded into testing system 100 less than about 4 hours after completion of the HERB process. For example, second holding member 416 is operated to move into first operational position 402. Plated samples 300 are then loaded into vise system 106 as described above for unplated samples 301, and second holding member 416 is moved to second operational position 404 at the rate of movement. After second holding member 416 is in second operational position 404, timing for the predetermined duration begins. A static load is applied to plated samples 300 at the predetermined percentage of their baseline ultimate failure distance (OBD) based on the calibration. More specifically, second holding member 416 is held at distance D that facilitates applying a static load at 75 percent of the baseline ultimate failure distance for unplated samples 301. Vise system 106 remains in second operational position 404 for the predetermined duration of time, and each plated sample 300 is analyzed after the predetermined duration of time has elapsed.

Vise system 106 is sized to receive any suitable number of plated samples 300 that enables testing system 100 to function as described herein. In the exemplary implementation, each vise system 106 is sized to receive up to three plated samples 300 simultaneously. In operation, the hydrogen embrittlement determination may be based on how many plated samples 300 fracture before expiration of the predetermined duration. For example, when none of the three plated samples 300 fracture before expiration of the predetermined duration, it may be an indication that hydrogen embrittlement has not occurred and that the plating solution used to fabricate that batch of plated samples 300 is not contaminated and/or embrittling. In another situation, for example, when only one of the three plated samples 300 fractures, it may be an indication of inconclusive results and that plated samples 300 should be re-tested. In yet another situation, for example, when a majority (e.g., two or three) of the three plates samples 300 fracture, it may be an indication that plated samples 300 have been impaired by hydrogen embrittlement and that the plating solution is contaminated and/or embrittling.

In some implementations, the predetermined duration of time used to determine whether hydrogen embrittlement has occurred is based on a number of factors. For example, the predetermined duration of time may be based on the dimensions of plated samples 300, the material used to fabricate plated samples 300, and the predetermined percentage of the baseline ultimate failure distance for plated samples 300 used during operation. In the exemplary implementation, the predetermined duration is about 8 hours.

Figure 7:
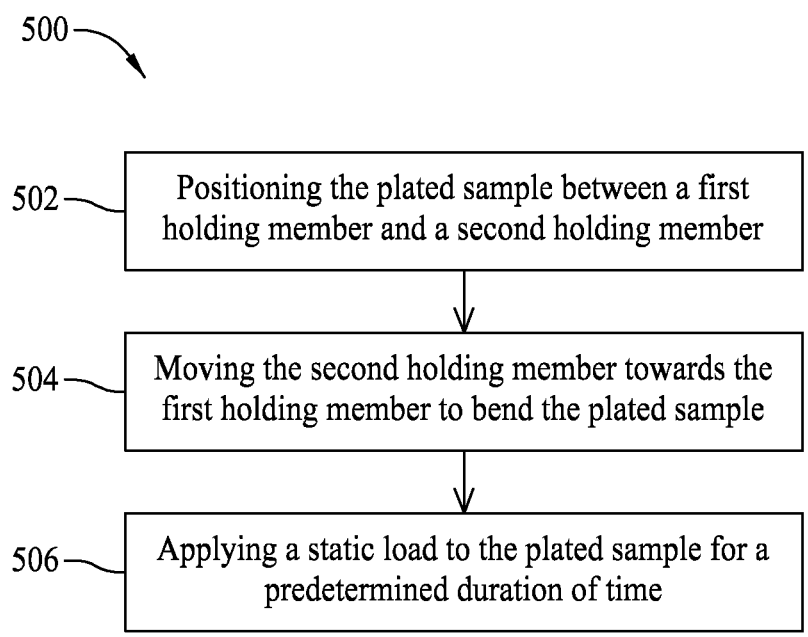
FIG. 7 is a flow diagram of an exemplary method for determining hydrogen embrittlement in a plated sample that may be used with the testing system shown in FIG. 1.

FIG. 7 is a flow diagram of an exemplary method 500 for determining hydrogen embrittlement in a plated sample. In the exemplary implementation, the plated sample is positioned 502 between a first holding member and a second holding member. The second holding member is moved 504 towards the first holding member to bend the plated sample. A static load is then applied 506 to the plated sample for a predetermined duration of time, where the static load is applied by bending the plated sample to a distance that is a predetermined percentage of a baseline ultimate failure distance of the plated sample.

The testing system and methods described herein facilitate determining the presence of hydrogen embrittlement in plated test samples, which enables a contamination level of an associated plating solution to be determined More specifically, the plated samples are loaded into the testing system, and a static load is applied to the samples by bending the plated sample to a distance that is a predetermined percentage of a baseline ultimate failure distance of the plated sample. The plated samples are fabricated in accordance with the specifications described herein such that a determination of the presence of hydrogen embrittlement may be made in real-time. More specifically, the testing system and methods described herein have been calibrated to enable the determination to be made in about 8 hours. As such, the contamination level of a plating solution may be determined in real-time, which may facilitate an increase in production of plated components.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for determining hydrogen embrittlement in a plated sample, said method comprising:
   positioning the plated sample between a first holding member and a second holding member;
   moving the second holding member towards the first holding member along an axis to bend the plated sample; and
   applying a static load to the plated sample for a predetermined duration of time, the static load applied by bending the plated sample out of plane with the axis when the first and second holding members are spaced an axial distance from each other, wherein the axial distance between the first and second holding members is selected to be a predetermined percentage of a baseline ultimate failure distance that causes a plurality of unplated samples to fracture.

2. The method in accordance with claim 1 further comprising inspecting the plated sample for an indication of fracture, wherein a fracture in the plated sample before expiration of the predetermined duration is used to determine a presence of hydrogen embrittlement.

3. The method in accordance with claim 1, wherein positioning the plated sample between a first holding member and a second holding member comprises bending the plated sample to fit within the axial distance defined between the first and second holding members that is less than a length of the plated sample.

4. The method in accordance with claim 1, wherein moving the second holding member towards the first holding member along an axis comprises moving the second holding member towards the first holding member substantially linearly along a translational axis.

5. The method in accordance with claim 1, wherein moving the second holding member towards the first holding member comprises moving the second holding member towards the first holding member at a rate of about 0.1 inch per minute.

6. The method in accordance with claim 1, wherein moving the second holding member towards the first holding member comprises selecting the distance such that the predetermined percentage is about 75 percent of the baseline ultimate failure load.

7. The method in accordance with claim 1, wherein applying a static load comprises selecting the predetermined duration based on at least one of dimensions of the plated sample, the predetermined percentage of the baseline ultimate failure distance, and materials used to fabricate the plated sample.

8. The method in accordance with claim 1, wherein applying a static load comprises maintaining the second holding member at a predetermined distance from the first holding member for the predetermined duration.

9. The method in accordance with claim 1 further comprising selecting a plated sample fabricated from an AISI 1095 steel substrate.

10. A system for determining hydrogen embrittlement in a plated sample, the system comprising:
    a frame;
    a first holding member coupled to said frame;
    a second holding member coupled to said frame and configured to move relative to said first holding member along an axis; and
    a testing location defined between said first and said second holding members, wherein said testing location receives the plated sample and said second holding member moves towards said first holding member to apply a static load to the plated sample by bending the plated sample out of plane with the axis when said first and said second holding members are spaced an axial distance from each other, wherein the axial distance between the first and second holding members is selected to be a predetermined percentage of a baseline ultimate failure distance that causes a plurality of unplated samples to fracture.

11. The system in accordance with claim 10 further comprising a control system configured to control a rate of movement of said second holding member towards said first holding member.

12. The system in accordance with claim 10 further comprising a timing device configured to determine a time of failure for the plated sample based on whether the plated sample fractures before expiration of a predetermined duration.

13. The system in accordance with claim 10, wherein said second holding member is slidably coupled to said frame to move towards said first holding member substantially linearly along a translational axis.

14. The system in accordance with claim 10 further comprising a protective cover positioned about said frame that is configured to block discharge of said plated sample from said testing location during fracture.

15. The system in accordance with claim 14, wherein said protective cover is configured to separate the plated sample from another plated sample when a plurality of plated samples are received within said testing location.

16. A system for determining hydrogen embrittlement, the system comprising:
    a frame;
    a first holding member coupled to said frame;
    a second holding member coupled to said frame and configured to move towards said first holding member along an axis; and
    a plated sample positioned between said first and said second holding members, wherein said plated sample bends when said second holding member moves towards said first holding member to apply a static load to said plated sample by bending said plated sample out of plane with the axis when said first and said second holding members are spaced an axial distance from each other, wherein the axial distance between the first and second holding members is selected to be a predetermined percentage of a baseline ultimate failure distance that causes a plurality of unplated samples to fracture.

17. The system in accordance with claim 16, wherein said plated sample is fabricated from an AISI 1095 metal substrate.

18. The system in accordance with claim 16, wherein said plated sample is fabricated using at least one of a cadmium solution and a zinc-nickel solution.

19. The system in accordance with claim 16, wherein said plated sample has a length of about 8 inch, a width of about 0.5 inch, and a thickness of about 0.03 inch.

20. The system in accordance with claim 16, wherein said plated sample comprises a notch defined within a surface thereof.

\* \* \* \* \*